United States Patent [19]

Young

[11] Patent Number: 5,569,580
[45] Date of Patent: Oct. 29, 1996

[54] METHOD FOR TESTING THE TOXICITY OF CHEMICALS USING HYPERACTIVATED SPERMATOZOA

[75] Inventor: Ronald J. Young, Columbia, Md.

[73] Assignee: The United States of America as represented by the Secretary of the Army, Washington, D.C.

[21] Appl. No.: 390,454

[22] Filed: Feb. 13, 1995

[51] Int. Cl.$^6$ .............................. A01N 1/02; C12Q 1/18
[52] U.S. Cl. .................................................. 435/2; 435/32
[58] Field of Search .................................... 435/2, 29, 32

[56] References Cited

U.S. PATENT DOCUMENTS

| | | | |
|---|---|---|---|
| 4,683,213 | 7/1987 | Ax | 436/501 |
| 4,767,703 | 8/1988 | Ax et al. | 435/29 |
| 5,250,417 | 10/1993 | Feuchter | 435/23 |

OTHER PUBLICATIONS

Young et al. Molecular Reproduction and Development 33: 347–356 (1992).
Brackett et al. Biology of Reproduction 12: 260–274 (1975).
GIBCO BRL Catalogue & Reference Guide.

Primary Examiner—Arthur L. Corbin
Attorney, Agent, or Firm—Ulysses John Biffoni; Edward L. Stolarun

[57] ABSTRACT

A method is provided for the in vitro testing of chemicals to determine reproductive toxicity using hyperactivated rabbit spermatozoa, and a method is provided for the in vitro production of said rabbit spermatozoa of hyperactivated motility useful in said testing. Spermatozoa are incubated in a simple salts medium in air at 22° to 37° C. Hyperactivated motility develops in one-half to one hour. Motility parameters are then measured using motion analysis systems and models for the classification of spermatozoa based on motility. Inhibition of hyperactivated motility of spermatozoa by exposure to chemicals may be used as an in vitro method of assessing the reproductive consequences of exposure of males to chemicals.

15 Claims, No Drawings

5,569,580

METHOD FOR TESTING THE TOXICITY OF CHEMICALS USING HYPERACTIVATED SPERMATOZOA

FIELD OF USE

A method is provided for the in vitro testing of chemicals to determine reproductive toxicity using hyperactivated spermatozoa. In addition, a method is provided for the in vitro production of rabbit spermatozoa of hyperactivated motility useful in said testing.

BACKGROUND OF THE INVENTION

This invention relates to a method for the in vitro testing of chemicals to determine reproductive toxicity, and a method for producing, in vitro, rabbit spermatozoa of hyperactivated motility useful in said testing.

The present invention provides a method for in vitro toxicity testing through exposure of hyperactivated spermatozoa to test chemicals and measuring the inhibition of hyperactivated motility. This invention also provides a process for producing spermatozoa of hyperactivated motility in one-half to one hour, thereby making it practical to perform said testing.

Development of alternative toxicological testing methods which do not require harm to animals is highly desirable in view of the current societal attitude towards the use of animals in experiments. Methods currently used to detect male reproductive toxicants are wanting in this respect in that they require the exposure of chemicals to large numbers of animals. Moreover, the methods used are time consuming and costly.

Spermatozoa are capable of fertilizing an egg only after undergoing a process in the female reproductive tract known as capacitation. An integral part of capacitation is the development by spermatozoa of hyperactivated motility, characterized by a low frequency, wide amplitude bending of the tail resulting in vigorous random and non-progressive movements. Development of hyperactivated motility is generally recognized as a prerequisite to fertilization. The inhibition of hyperactivity by xenobiotics indicates the xenobiotic will adversely affect fertility.

Any chemical that adversely affects spermatozoan motility is suspect as a reproductive toxicant which may prevent fertilization. Measurement of the extent of hyperactivated motility development in spermatozoa in the presence of chemicals provides a means for the in vitro assessment of the chemical's potential to cause male fertility disturbances.

The invention described herein employs a simple salts medium and incubation protocol which induces hyperactivated motility in spermatozoa in one-half to one hour. Motility parameters are then measured using existing motion analysis systems such as CellSoft or CellTrak, and using previously formulated models for classification of spermatozoa, the extent of hyperactivation development in the presence or absence of the test chemical is computed. The ability to objectively recognize hyperactivated spermatozoa enables the measurement of hyperactivated motility inhibition by chemicals. This in vitro method is faster and more economical than traditional animal testing methods and does not harm or expose animals to chemicals.

SUMMARY OF THE INVENTION

The present invention provides a method for in vitro testing of chemicals to determine reproductive toxicity.

The method for in vitro testing comprises the steps of forming a suspension of hyperactivated spermatozoa, exposing the suspension to a chemical whose reproductive toxicity is to be determined, and monitoring any change in hyperactivity of the spermatozoa in the suspension.

In a preferred embodiment, the suspension of hyperactivated spermatozoa is formed by incubating the spermatozoa in a buffered salt medium for about one-half to one hour, in ambient air, in essentially ambient temperatures. The buffered salt medium is comprised of mixtures of alkali metal—halogen salts and/or alkaline earth metal—halogen salts, glucose, bovine serum albumen, and a buffer. In an especially preferred embodiment, the suspensions of hyperactivated spermatozoa are rabbit spermatozoa and the buffered medium comprises: KCl 30 mg; $CaCl_2 2H_2O$ 33 mg; $MgCl_2 6H_2O$ 10.6 mg; NaCl 759 mg; Tris HCl 57.2 mg; Tris 16.6 mg; bovine serum albumen 300 mg; and glucose 250 mg; all per 100 ml of water.

The samples may be divided into a multiplicity of sub-samples, out of which a control may be reserved.

In another embodiment of the test, sperm cells are exposed to different concentrations of the test chemical. Motility patterns of the spermatozoa are then observed and recorded using motion analysis systems and models for classification of the spermatozoa based on motility. The motility patterns of the chemically exposed spermatozoa are compared to those of an unexposed control sample.

The measurement of the inhibition of hyperactivated motility by the test compounds is the basis for determining the chemical's reproductive toxicity.

The invention also provides a method for rapid in vitro development of spermatozoa having hyperactivated motility. This method uses the buffered salt medium described above for incubating spermatozoa in suspension for about 0.5 to 1.0 hour in ambient air at temperatures ranging from about 22° C. to about 37° C. This method of inducing hyperactivated spermatozoa is an important step in the toxicity test also disclosed herein.

DESCRIPTION OF THE PREFERRED EMBODIMENTS

The present invention relates to a method of in vitro testing of chemicals to determine reproductive toxicity and a method for rapidly producing spermatozoa of hyperactivated motility useful in said testing. The new method of reproductive toxicity testing is faster and more economical than traditional methods, and does not require exposing animals to chemicals or harmful stimuli or handling. This method also generates little hazardous waste.

The reproductive toxicity test and the method of in vitro production of spermatozoa of hyperactivated motility of the invention are expected to be applicable to mammalian spermatozoa and to other classes of animals and fish. In experiments performed to establish the processes and utility of the invention, rabbit spermatozoa were selected as the vehicle for the in vitro test system. This choice was made because rabbit spermatozoa are representative of the spermatozoa of other mammals and also other classes of animals and fish. In addition, the rabbit is commonly used in many toxicological studies, they are readily available, easily maintained under controlled conditions, and their spermatozoa can be obtained without harming the animal. Capacitation in vitro can be achieved by the procedure of Brackett and Oliphant (Biology of Reproduction, 12:260 [1975]) (incorporated by reference herein) in which spermatozoa are preincubated in a high ionic strength medium, then incubated in a defined medium under atmosphere of 8% $O_2$, 5% $CO_2$ and 87% $N_2$ at 37° C. Rabbit spermatozoa so treated develop hyperactivated motility after 16 hours of incubation.

The motility parameters of hyperactivated spermatozoa are measured with two commercially available motion analysis systems known as CellSoft™ and Celltrak™. By applying multivariate discriminant and associated regression analysis with a classification method, models for classifying motile spermatozoa into hyperactivated and nonhyperactivated classes were formulated. The ability to objectively recognize hyperactivated rabbit spermatozoa allows for the measurement of hyperactivated motility inhibition by chemicals being tested for possible reproductive toxicity. This, together with the in vitro rabbit spermatozoan hyperactivation system can be the basis for an in vitro method of fertility testing in which animals are not exposed to potentially toxic chemicals or harm. The 16 hour incubation period required for hyperactivating spermatozoa is an inconvenience and an impediment to the development of a practical fertility testing method. The method for in vitro production of spermatozoa having hyperactive motility disclosed herein overcomes this limitation.

The method of production, hitherto unavailable, allows for the rapid development in vitro of spermatozoa of hyperactivated motility. Spermatozoa are incubated in a simple salts medium exposed to ambient air at roughly ambient temperatures ranging from about 22° C. to about 37° C. Incubation of spermatozoa in the simple salts medium of the method disclosed herein is a convenient, practical and expeditious way to induce hyperactivated motility in spermatozoa and serves as a key step in the method for reproductive toxicity testing in vitro.

The method of production employs a new medium and incubation protocol for inducing the hyperactivated motility of spermatozoa in about 0.5 to 1.0 hour. The medium, more particularly described below in the experimental section, is comprised of a mixture of alkali metal-halogen salts and alkaline earth metal-halogen salts, glucose, bovine serum albumen and a buffer. Centrifugation and incubation procedures are described below.

EXAMPLES

Method of Inducing Hyperactivation of Sperm Cells. Rabbit semen is collected in an artificial vagina, and purified as described in Molecular Reproduction and Development vol 33, p347, 1992. This volume is incorporated by reference herein. The semen sample from one rabbit is layered on top of a discontinuous Percoll density gradient composed of solutions of Percoll in buffer A, and centrifuged for 10 minutes at 500 g at room temperature in a swing-out rotor. The gradient composition is 90% (v/v) 1 part; 65% (v/v) 1 part; 50% (v/v) 4 parts. Buffer A final concentration in each layer is 4 mM KCl, 2.25 mM $CaCl_2$, 0.52 mM $MgCl_2$, 130 mM NaCl, 2.5 mg/ml glucose, 1 mg/ml bovine serum albumen and 5 mM HEPES, pH 7.4. The 65% and 90% Percoll layers are combined, diluted with 4 volumes of warm (37° C.) medium M and centrifuged at 350 g for 5 minutes at room temperature. The sperm pellet formed by centrifugation is gently resuspended in warm medium M and centrifugation repeated. The resulting sperm pellet is gently resuspended in medium M at a concentration of 5 to $10\times10^6$ cells/ml and incubated at 37° C. Hyperactivated spermatozoa appear after one-half to one hour incubation and remain for two to four hours. Medium M is KCl 30 mg, $CaCl_2.2H_2O$ 33 mg, $MgCl_2.6H_2O$ 10.6 mg, NaCl 759 mg, Tris.HCl 57.2 mg, Tris 16.6 mg, bovine serum albumen 300 mg, and glucose 250 mg per 100 ml water. Tris and Tris.HCl may be replaced by HEPES 119 mg/100 ml and the pH adjusted to 7.4 with HCl.

Exposure to Chemicals. Culture tubes containing suspensions of sperm cells (5 to $10\times10^6$ cells/ml) and the test chemical are placed in a rack inclined at an angle of 15° and incubated at 37° C. Sperm cells are exposed to at least three different concentrations of the test chemical. A culture tube containing only sperm cells is included as a control sample. At time intervals, the control and exposed sperm suspensions are gently stirred and a 5 microliter drop is removed from each for videotaping. The 5 microliter drop is placed in a prewarmed 20 micrometer deep chamber, the chamber covered with a coverslip and placed on the warm (37° C.) microscope stage. A minimum of seven random microscope fields are videotaped for 10 to 15 seconds at 30 frames per second. At least two drops of the sperm suspensions are removed for videotaping.

Hardware for Videotaping Analysis. The components for videotaping motility patterns of spermatozoa were as follows: A Dage NC-67M videocamera mounted on an Olympus BH-2 microscope equipped with a 10× negative phase contrast objective, a 6.7× projection ocular and a warming stage heated to 37° C. Video images are recorded on a Sony VO-5800 or a Panasonic AG 6300 video recorder attached to a VTG-33 For.A time generator and a VTW-100 For.A video typewriter to permit recording of elapse time and identification of the tape segment.

The motility parameters of the spermatozoa are measured by either CellSoft or CellTrak motion analysis systems. For the CellSoft system, the CellSoft proprietary hardware and software are installed in a computer configured and equipped with peripherals to match the specifications of the manufacturer (Cryo Resources, Ltd). Playback and display of the digitized images are observed on two Panasonic WV-5410 video monitors. The CellTrak system is supplied as a single integrated unit (Motion Analysis Corp.) and used as such.

Videotaping. A 5 microliter drop of sperm suspension is placed in a prewarmed chamber about 20 micrometers deep, the chamber is covered with a cover slip and placed on the warm (37° C.) microscope stage. A minimum of 7 random microscope fields are videotaped for 10–15 seconds at 30 or 60 frames/second. At least two drops of the sperm suspensions are removed for videotaping.

Motility Analysis. Software settings recommended by the manufacturer of the motion analysis systems are used for the analysis of the motion characteristics of spermatozoa recorded on videotape. To accommodate the rapid and random motions of hyperactivated rabbit spermatozoa, software settings specific for analysis of hyperactivated rabbit spermatozoa are necessary for the CellSoft system. These settings are linearity 0, size range 1–120 pixels, and maximum velocity 500–1200 micrometers/second. The settings for analysis of rabbit spermatozoa by the CellTrak system are centroid size range 2–25 pixels, ALH path smoothing factor 7 and velocity range 20–500 micrometers/second, and are used for both hyperactivated and nonhyperactivated spermatozoa. A one second segment of each of the seven fields from each of two drops are tracked at a frame rate of 30 or 60 frames/sec for computation of the motility parameters. Motility parameters are measured for a minimum off 200 spermatozoa.

Data Analysis. Analysis of the sperm motion is carried out as described above to determine the motility parameters linearity (LIN), curvilinear velocity (VCL), wobble (WOB), and average amplitude of lateral head displacement (AALH), for all spermatozoa in each field at each time period sampled for the control, and spermatozoa exposed to the three concentrations of the test compound. Spermatozoa are classified into hyperactivated and nonhyperactivated classes based on the motility parameters WOB and VC according to the following criteria: for analysis performed with the CellSoft system at 30 frames/second, spermatozoa are hyperactivated if WOB is less than or equal to 0.78 and VCL is greater than or equal to 51 micrometers/sec. The criteria for analysis performed on the CellTrack system at 30 frames/second are: hyperactivated if WOB is less than or equal to 0.69 and VCL is greater than or equal to 55 micrometers/sec. The percentage of hyperactivated spermatozoa in the controls and in the exposed samples is calculated. Analysis of variance can be used to determine if exposure to the test compound inhibited development of hyperactivated motility in a time and concentration manner. It was shown using this protocol that $Pb^{+2}$, as $PbCl_2$, and $Cd^{+2}$, as $CdCl_2$, two metals suspected of causing male infertility in humans, inhibited development of hyperactivated motility. $Cr^{+6}$, as $K_2Cr_2O_7$, was found not to inhibit hyperactivity. Two metals not implicated in male fertility disturbances, $Hg^{+2}$ and $Zn^{+2}$, had no effect on the development of hyperactivated motility in rabbit spermatozoa.

To a person of ordinary skill in the art to which this invention pertains many modifications and variations will suggest themselves. Such modifications and variations are therefore within the scope of this invention.

What is claimed is:

1. A method of determining the reproductive toxicity of a chemical, comprising the steps of:
   (a) forming a suspension of hyperactivated spermatozoa;
   (b) exposing said suspension to the chemical; and
   (c) monitoring the change in hyperactivity of the spermatozoa and determining reproductive toxicity based on any inhibition of said hyperactivity.

2. The method of claim 1, wherein said suspension of hyperactivated spermatozoa is formed by incubating the spermatozoa in a buffered salt medium.

3. The method of claim 2, wherein said spermatozoa are rabbit spermatozoa and said buffered medium comprises: about 4 mM KCl; about 2.25 mM $CaCl_2$ $2H_2O$; about 0.52 mM $MgCl_2$ $6H_2O$; about 130 mM NaCl; about 14 mM glucose; about 50 mM Tris; and about 3 mg/ml bovine serum albumen.

4. The method of claim 3, wherein Tris of the buffered salt medium is replaced by HEPES at about 9 mg per 100 ml $H_2O$ and pH is adjusted to about 7.4.

5. The method of claim 1, wherein:
   a. said suspension is divided into a plurality of samples;
   b. each sample is exposed to a different concentration of the test chemical; and
   c. each sample is monitored for change in hyperactivity of the spermatozoa.

6. The method of claim 5, wherein a control sample which is not exposed to the test chemical is also maintained.

7. The method of claim 5, wherein a plurality of subsamples are removed from said plurality of exposed samples at time intervals and monitored for change in hyperactivity of the spermatozoa.

8. The method of claim 7, wherein said monitoring is conducted by measuring the motility parameters of the spermatozoa.

9. The method of claim 8, wherein said motility parameters include linearity, curvilinear velocity, wobble, and average amplitude of lateral head displacement.

10. The method of claim 8, wherein said motility parameters are measured using automated computer-assisted digital image motion analysis systems.

11. The method of claim 1, further comprising:
    a. exposing said suspension to the chemical at a given concentration;
    b. monitoring the change in hyperactivity of the spermatozoa in said suspension;
    c. increasing the concentration of the chemical in said suspension; and
    d. monitoring the change in hyperactivity of the spermatozoa in said suspension of increased chemical concentration.

12. The method of claim 11, wherein subsamples are removed from said suspension at time intervals after exposure to the chemical at a given concentration and monitored for change in hyperactivity.

13. The method of claim 12, wherein said monitoring is conducted by measuring the motility parameters of the spermatozoa.

14. The method of claim 13, wherein said motility parameters include linearity, curvilinear velocity, wobble, and average amplitude of lateral head displacement.

15. The method of claim 13, wherein said motility parameters are measured using automated computer-assisted digital image motion analysis systems.

* * * * *